United States Patent
Kaneda (10) Patent No.: US 7,757,564 B2
(45) Date of Patent: Jul. 20, 2010

(54) MATERIAL TESTING MACHINE

(75) Inventor: Masaki Kaneda, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 41 days.

(21) Appl. No.: 12/304,331

(22) PCT Filed: Jun. 12, 2006

(86) PCT No.: PCT/JP2006/311731

§ 371 (c)(1),
(2), (4) Date: Dec. 11, 2008

(87) PCT Pub. No.: WO2007/144928

PCT Pub. Date: Dec. 21, 2008

(65) Prior Publication Data

US 2009/0199663 A1    Aug. 13, 2009

(51) Int. Cl.
*G01N 3/00* (2006.01)
(52) U.S. Cl. .......................... 73/796; 73/760
(58) Field of Classification Search ............ 73/760–796
See application file for complete search history.

(56) References Cited

U.S. PATENT DOCUMENTS

| | | | | |
|---|---|---|---|---|
| 4,478,086 A | * | 10/1984 | Gram | 73/781 |
| 4,531,901 A | * | 7/1985 | Andersen | 425/150 |
| 4,828,769 A | * | 5/1989 | Maus et al. | 264/1.31 |
| 5,092,179 A | * | 3/1992 | Ferguson | 73/790 |
| 5,413,306 A | | 5/1995 | Mahoney, III et al. | |
| 5,677,494 A | * | 10/1997 | Keener et al. | 73/810 |
| 7,137,306 B2 | * | 11/2006 | Ferguson et al. | 73/818 |
| 7,353,715 B2 | * | 4/2008 | Myers | 73/837 |
| 2010/0011873 A1 | * | 1/2010 | Kaneda | 73/788 |

FOREIGN PATENT DOCUMENTS

| | | |
|---|---|---|
| JP | 7-35665 A | 2/1995 |
| JP | 9-292320 A | 11/1997 |

OTHER PUBLICATIONS

International Search report of PCT/JP2006/311731, date of mailing Aug. 29, 2006.

* cited by examiner

*Primary Examiner*—Max Noori
(74) *Attorney, Agent, or Firm*—Westerman, Hattori, Daniels & Adrian, LLP (57) ABSTRACT

The present invention includes: a pair of columnar members 12 disposed on both sides of a specimen piece SP; a crosshead 15, bridging the pair of columnar members 12, that applies a load to the specimen piece SP by moving in a direction of a longitudinal axis of the columnar member 12 and; a movable member 31 disposed at a side of the columnar member 12, extending in the direction of the longitudinal axis and elastically supported so as to be movable in the direction of the longitudinal axis; a striker 35, integrally attached to the movable member 31 so as to be displaceable in the direction of the longitudinal direction, that is allowed to be pushed by a movement of the crosshead 15 to a position where the striker is attached; a position sensor 38 that detects a movement of the movable member 31 by being pushed by the striker 35; a limitation member 34 that limits the position where the striker 35 is attached; and an elastic member 36 that supports the striker 35 so that the striker 35 is capable of relative movement in the direction of the longitudinal axis relative to the movable member 31 by a predetermined extent from a position limited by the limitation member 34.

10 Claims, 9 Drawing Sheets

MATERIAL TESTING MACHINE

TECHNICAL FIELD

The present invention relates to a material testing machine that applies a load to a test piece through a crosshead.

BACKGROUND ART

Conventionally, a testing machine is known in which right and left driving screws for elevating a crosshead are driven by the motor to elevate the crosshead to exert a test force on a test piece and the test piece is evaluated (for instance, see Patent Document 1). In this kind of testing machine, there is provided an automatic stop device in order to stop the crosshead at an arbitrary position. In, for instance, the testing machine described in Patent Document 1, a movable member is elastically supported on a side of a screw pole such that it can move in the longitudinal direction. Strikers are attached to the movable member such that their positions can be adjusted in the longitudinal direction. The movement of the movable member is detected by the position sensor. When the crosshead collides with the striker while the crosshead is elevating, the movable member is pushed and a signal indicating that the crosshead has reached the arbitrary position is output from the position sensor to automatically stop the crosshead. To return to the original state from the automatically stopped state, the striker is caused to become spaced apart from the crosshead to return the movable member to the original position.

Patent Document 1: Japanese Laid-Open Patent Application No. H09-292320

SUMMARY OF THE INVENTION

Problem to be Solved by the Invention

In this kind of testing machine, upper and lower limitation positions are set in advance as intrinsic values of the testing machine and the striker is disposed so as to be movable within the limitation positions. However, for instance, when the striker collides with the crosshead when the striker is set to the lower limitation position and the motor is automatically stopped, the striker will not be readily spaced apart from the crosshead since the downward movement of the striker is limited. As a result, it takes time to return from the automatically stopped state to the original state.

Means for Solving the Problem

A material testing machine according to the present invention is characterized by including: a pair of columnar members disposed on both sides of a specimen piece; a crosshead, bridging the pair of columnar members, that applies a load to the specimen piece by moving in a direction of a longitudinal axis of the columnar member; a movable member disposed at a side of the columnar member, extending in the direction of the longitudinal axis and elastically supported so as to be movable in the direction of the longitudinal axis; a striker, integrally attached to the movable member so as to be displaceable in the direction of the longitudinal direction, that is allowed to be pushed by a movement of the crosshead to a position where the striker is attached; a position sensor that detects a movement of the movable member by being pushed by the striker; a limitation member that limits the position where the striker is attached; and an elastic member that supports the striker so that the striker is capable of relative movement in the direction of the longitudinal axis relative to the movable member by a predetermined extent from a position limited by the limitation member.

It is preferable to include an automatic stop means for automatically stopping the crosshead when the movement of the movable shaft is detected by the position sensor.

It is also possible that the limitation member is locked to the movable shaft with a tool to be disposed to a limitation position of an automatic stop position of the crosshead, and the elastic member is disposed between the crosshead and the striker or between the striker and the restriction member.

As the automatic stop means, a relay switch inserted in a motor power supply circuit may automatically stop the crosshead by opening the relay switch.

A pole cover that covers both the columnar member and the movable shaft may be provided, and the striker may be provided with an operation member with which the striker is operated, the operation member penetrating through the pole cover.

In this case, it is preferable that the operation member is a fastening member by which the striker is locked.

ADVANTAGEOUS EFFECT OF THE INVENTION

According to the present invention, the strikers are disposed such that they are movable relative to the movable member by a predetermined extent from the limitation positions. As a result, when the crosshead collides with the striker disposed at the limitation position to cause the crosshead to automatically stop, the striker can be spaced apart from the crosshead, so that the operation of returning from the automatically stopped state is easy to perform.

EXPLANATION OF SYMBOLS

12 Screw pole
15 Crosshead
25 Pole cover
31 Movable shaft
34 Restriction member
35 Striker
35a Bolt
36 Elastic body
38 Position sensor
43 Relay

BEST MODE FOR CARRYING OUT THE INVENTION

The following is an explanation of a material testing machine according to an embodiment of the present invention, given in reference to FIGS. 1 to 9.

Figure 1:
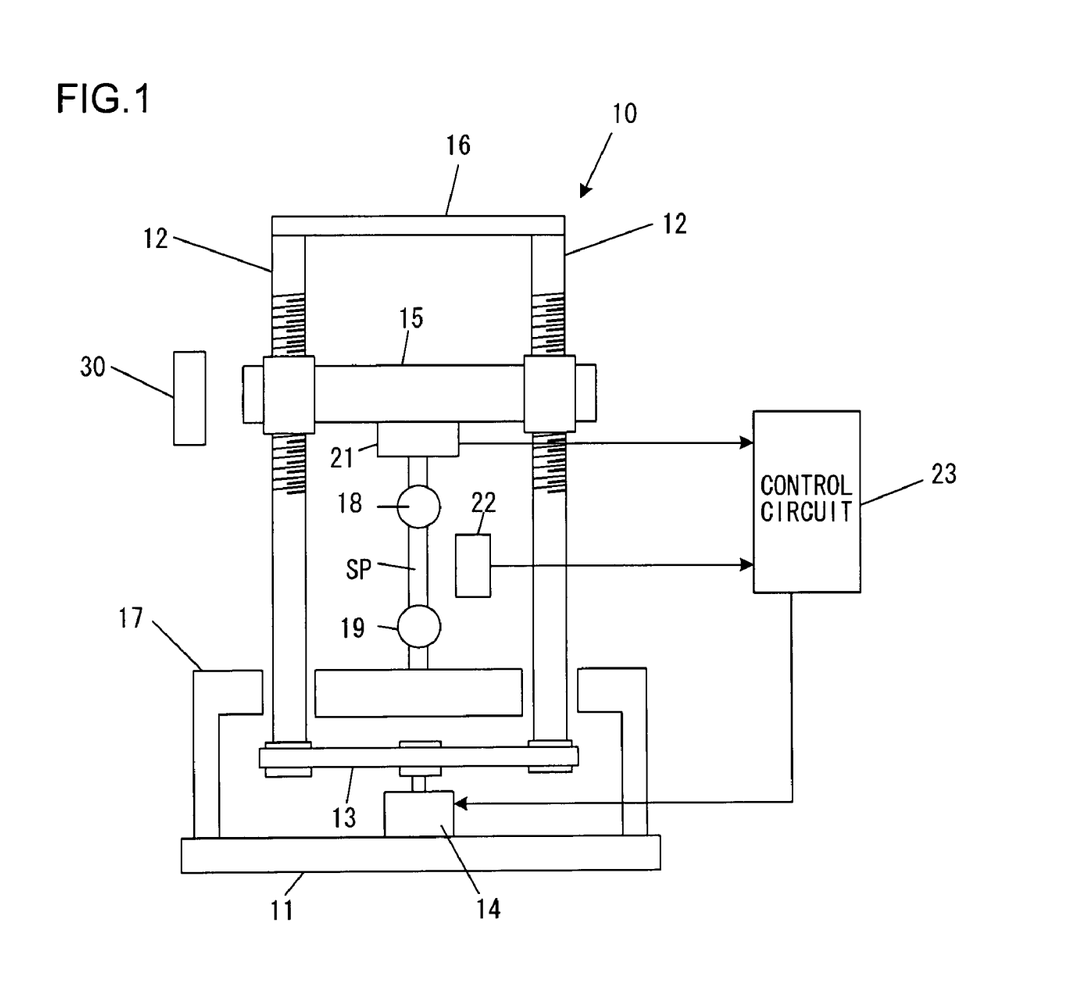
FIG. 1 is a schematic configuration diagram showing a material testing machine according to an embodiment of the present invention.

FIG. 1 is a schematic configuration diagram showing the material testing machine according to the present embodiment. A main body 10 of the testing machine includes a base 11, a pair of screw poles 12 that is set up on the base 11, a timing belt 13, a motor 14 that is mounted on the base 11 and rotates the screw pole 12 through the timing belt 13, a crosshead 15 elevatably held by the screw pole 12, a yoke 16 that bridges top ends of the screw poles 12, a table 17, upper and lower grippers 18, 19 that grip a specimen piece SP between the crosshead 15 and the table 17, and a position detection device 30 that detects that the crosshead 15 has arrived at a predetermined position.

The specimen piece SP has an upper part that is gripped by the upper grip 18 through a load cell 21 and a lower part that is gripped by the lower grip 19. The test force added onto the specimen piece SP is detected by the load cell 21, and displacement between top and bottom gage marks of the specimen piece SP is detected by a displacement gauge 22. Signals from the load cell 21 and the displacement gauge 22 are input to a control circuit 23. The material testing is performed by controlling the driving of the motor 14 according to a signal from the control circuit 23. On this occasion, a stop signal is output to the motor 14 when the movement of the crosshead 15 to a predetermined position is detected by the position detection device 30. As a result, the elevation of the crosshead 15 is automatically stopped.

Figure 2:
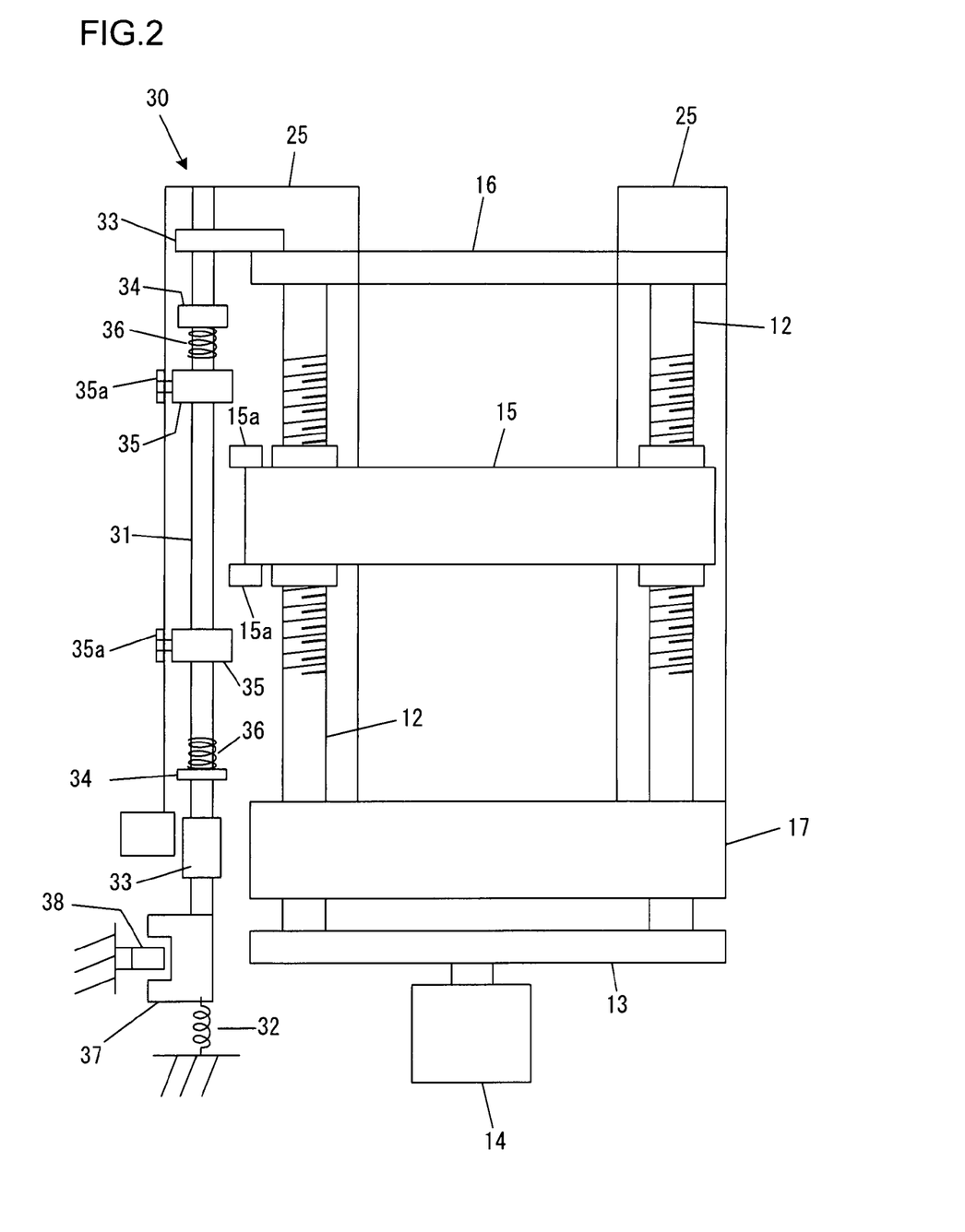
FIG. 2 is a diagram showing a main part of the machine of FIG. 1.

FIG. 2 is a front view of the main body 10 of the material testing machine, mainly showing the structure of the position detection device 30. Around the screw poles 12, there are set upright pole covers 25 for preventing dust and dirt from entering thereinto. Inside one of the pole covers 25, a movable shaft 31 is set upright in parallel to the screw pole 12. The movable shaft 31 is elastically supported on the base 11 through a spring 32 and is vertically slidable along respective guides 33 formed in the yoke 16 and the table 17.

A pair of strikers 35 vertically arranged sandwiching the crosshead 15 is attached to the movable shaft 31 such that they are slidable along the movable shaft 31. The strikers 35 arbitrarily set the automatic stop position of the crosshead 15. Positions at which the strikers 35 are attached are set appropriately according to the size of the specimen piece SP and contents of the testing on the specimen piece SP. The strikers 35 are locked to the movable shaft 31 by bolts 35a that penetrate through the pole cover 25.

Figure 3:
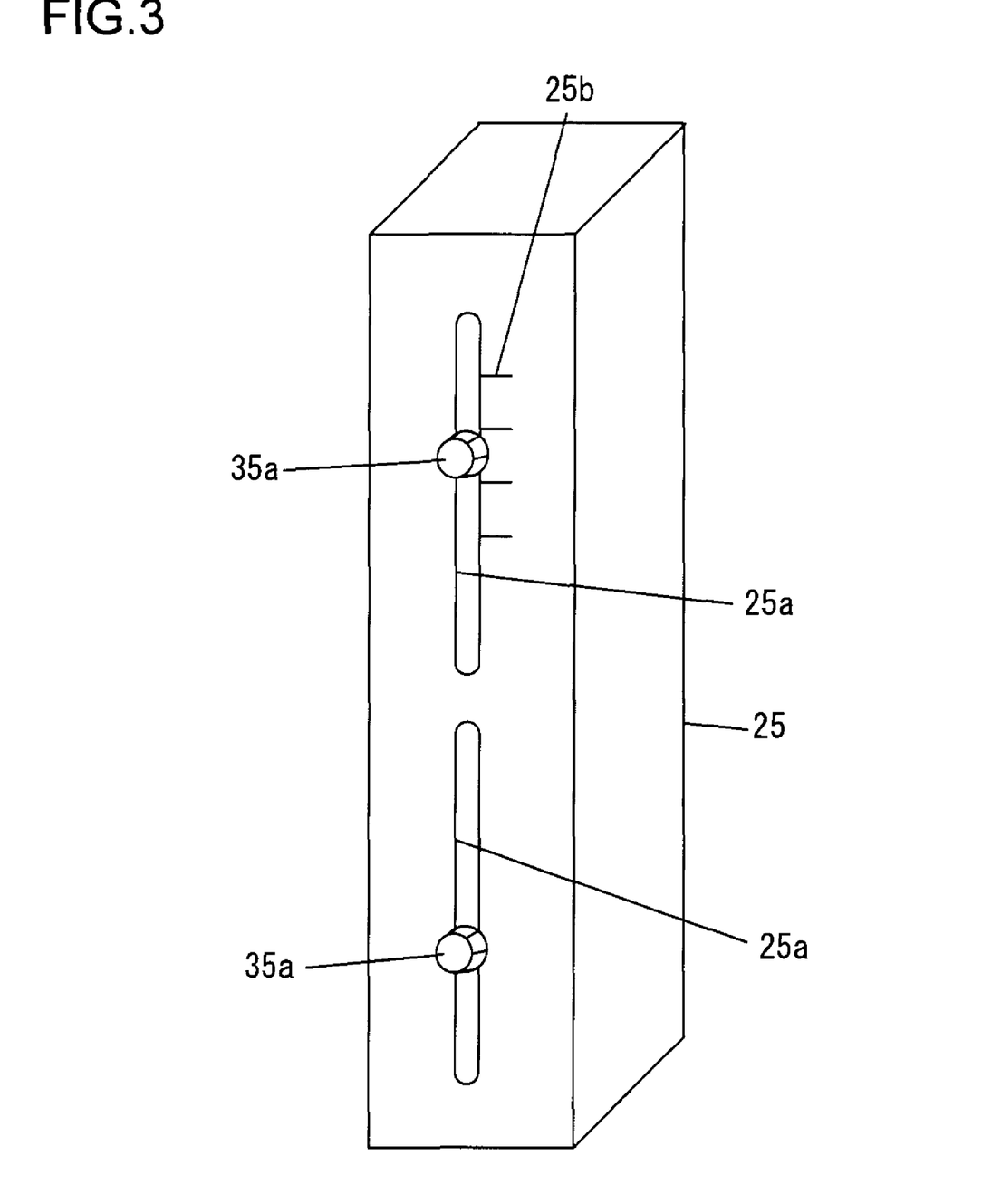
FIG. 3 is a perspective view seen from outside of the pole cover of FIG. 2.

Slits 25a are vertically formed in the pole cover 25 corresponding to the positions of bolts 35a as shown in FIG. 3, and the positions of the strikers 35 can be changed by vertically sliding the bolts 35a according to the slits 25a. The pole cover 25 is provided with indicators 25b that correspond to the automatic stop positions of the crosshead 15 upon various tests.

In addition, the movable shaft 31 is provided with a pair of restriction members 34 vertically arranged so as to sandwich the pair of strikers 35 vertically arranged as shown in FIG. 2. The restriction members 34 are disposed at parts corresponding to upper and lower bound positions, respectively, of the crosshead 15 and restrict the movement of the strikers 35. The upper and lower bound positions of the crosshead 15 are provided for as values (limitation positions) peculiar to the testing machine in order to prevent, for instance, interferences of the crosshead 15 with the yoke 16 and the table 17 that are superjacent and subjacent, respectively, the crosshead 15 and damages of other parts. Since the restriction members 34 are fastened to the movable shaft 31 by bolts and nuts or the like such that their attachment positions can not be changed arbitrarily and the restriction members 34 are disposed in a narrow space inside the pole cover 25, the user can not easily operate the restriction members 34.

An elastic body 36 is interposed between each of the upper and lower restriction members 34 and the striker 35. The elastic body 36, which is, for instance, a coil spring, is supported at one end thereof by the restriction member 34. The positions of the strikers 35 when they are brought into contact with the other end of the elastic bodies 36 correspond to the upper and lower bound positions of the crosshead 15. The elastic body 36 has a spring constant that is set greater than that of the spring 32 that supports the movable shaft 31.

When a pad 15a on an upper or a lower surface of the crosshead 15 collides with the striker 35 as a result of the elevation operation of the crosshead 15, the movable shaft 31 is pushed up or down against a biasing force urged thereon by the spring 32. A dog 37 of a substantially U-shape is integrally provided to the movable shaft 31 at a lower end thereof and a position sensor 38 is mounted on the base 11 corresponding to this dog 37. The dog 37 may be provided at a portion other than the lower end of the movable shaft 31 as far as it is integral to the movable shaft 31. The position sensor 38 may be attached to the pole cover 25 or the table 17 depending on the position at which the dog 37 is attached.

Figure 4:
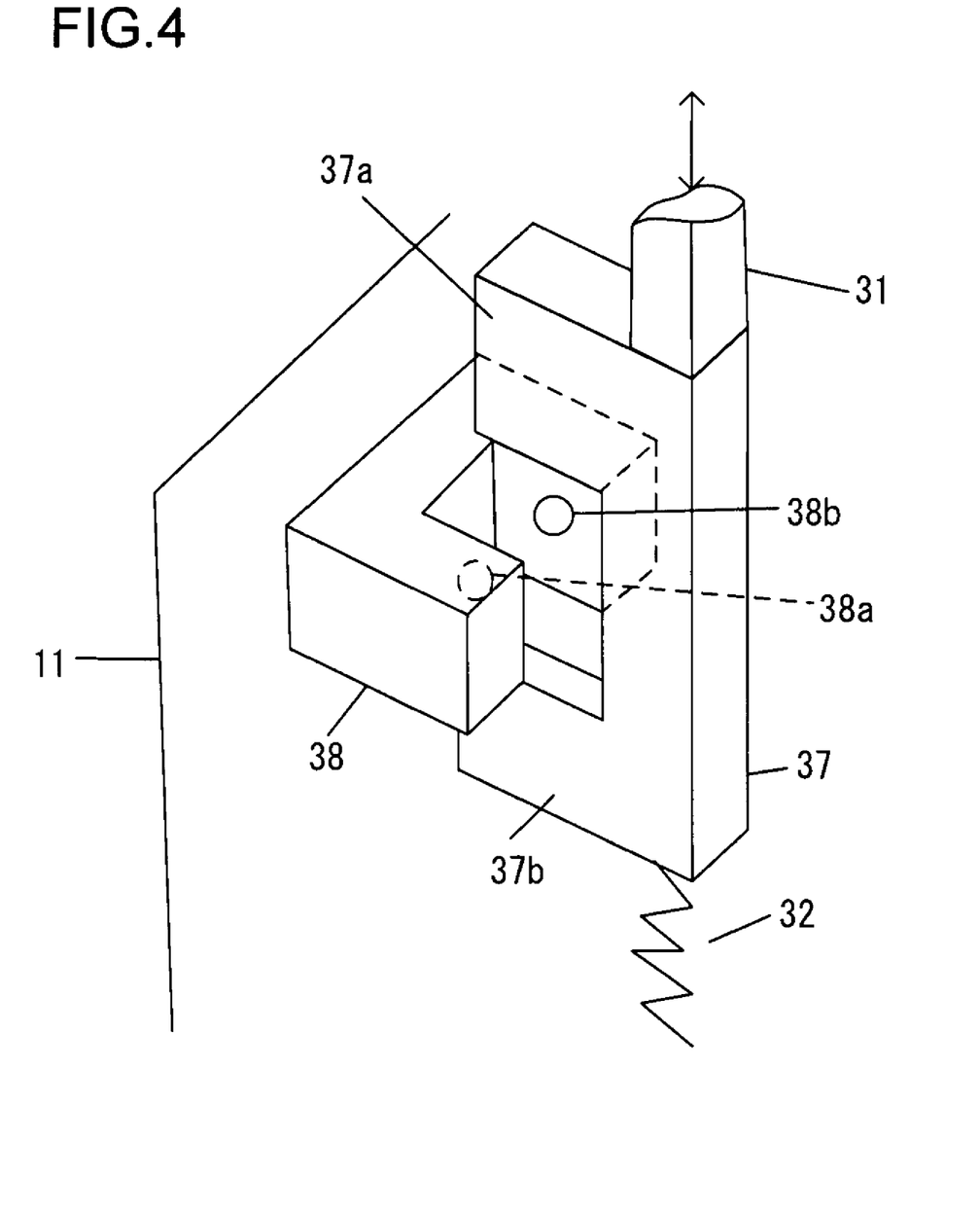
FIG. 4 is a perspective view of a position sensor of FIG. 2.

The position sensor 38 is, for instance, a photo interrupter. In an initial state, light from a floodlight projector 38a passes across the U-shape portion of the dog 37 and is received by a light receiving unit 38b. On this occasion, the sensor 38 outputs an ON signal. When the movable shaft 31 moves upward and the light from the floodlight projector 38a is interrupted by a lower part 37b of the dog 37, or when the movable shaft 31 moves downward and the light from the floodlight projector 38a is interrupted by an upper part 37a of the dog 37, the sensor 38 outputs an OFF signal. The signal from the position sensor 38 is input into the control circuit 23 (FIG. 1).

Figure 5:
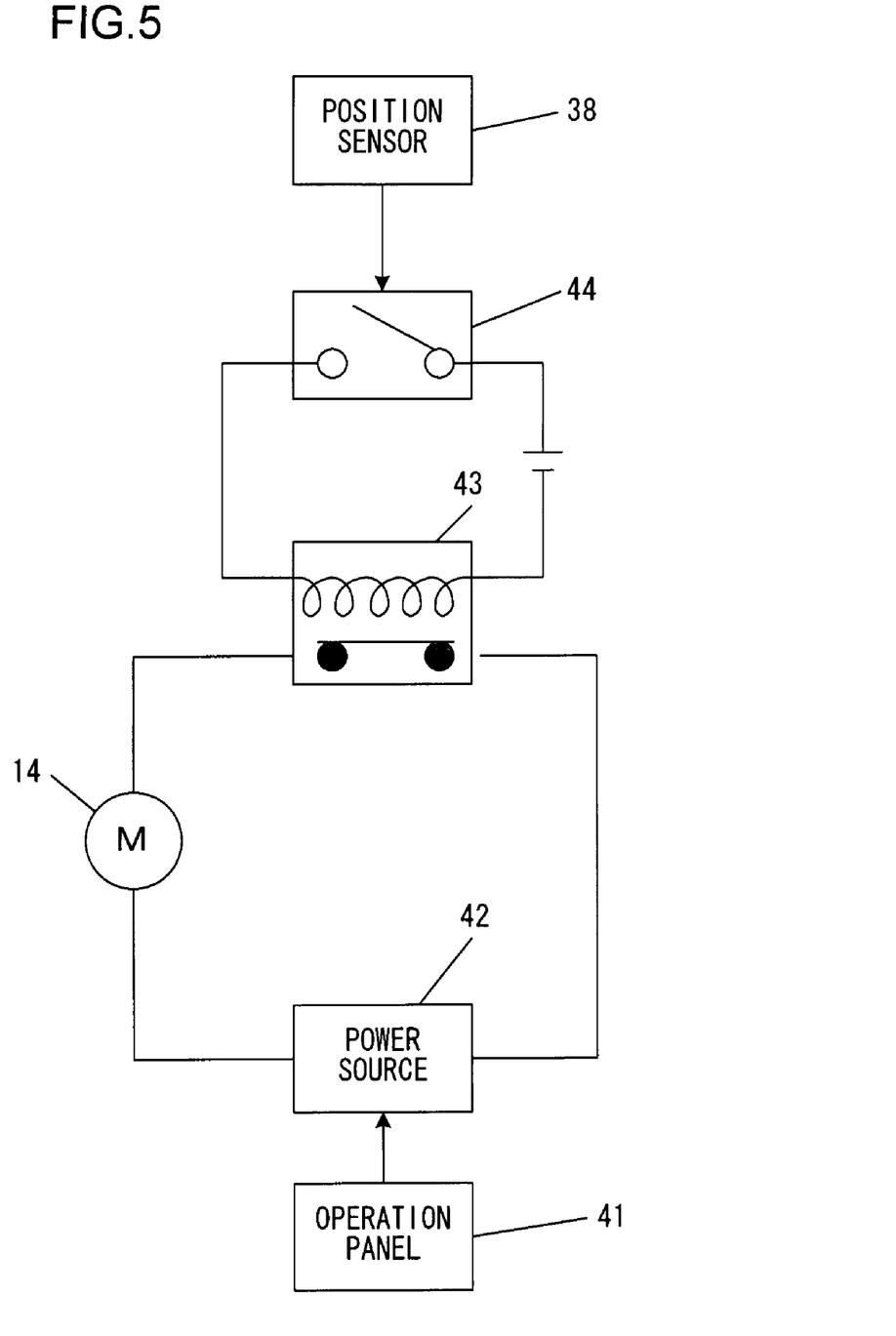
FIG. 5 is an electrical circuit diagram of a motor for driving a crosshead.

FIG. 5 is an electrical circuit diagram of the motor 14 that constitutes a part of the control circuit 23. An operation panel 41 is operated by the user to instruct raising, lowering, and stopping of the crosshead 15. When an instruction for raising or lowering the crosshead 15 is output from the operation panel 41, power is supplied from a power source 42 to the motor 14 to cause normal rotation or reverse rotation of the motor 14.

A relay 43 that has a normally-closed contact is disposed in the motor power supply circuit, and a switch 44 that switches in response to an ON/OFF signal of the position sensor 38 is connected to a coil of the relay 43. The switch 44 is turned OFF in response to an ON signal from the position sensor 38 and turns ON in response to an OFF signal from the position sensor 38. As a result, the motor 14 can be automatically stopped according to the signal from the position sensor 38.

The main operations of the material testing machine according to this embodiment are described below.

Figure 6:
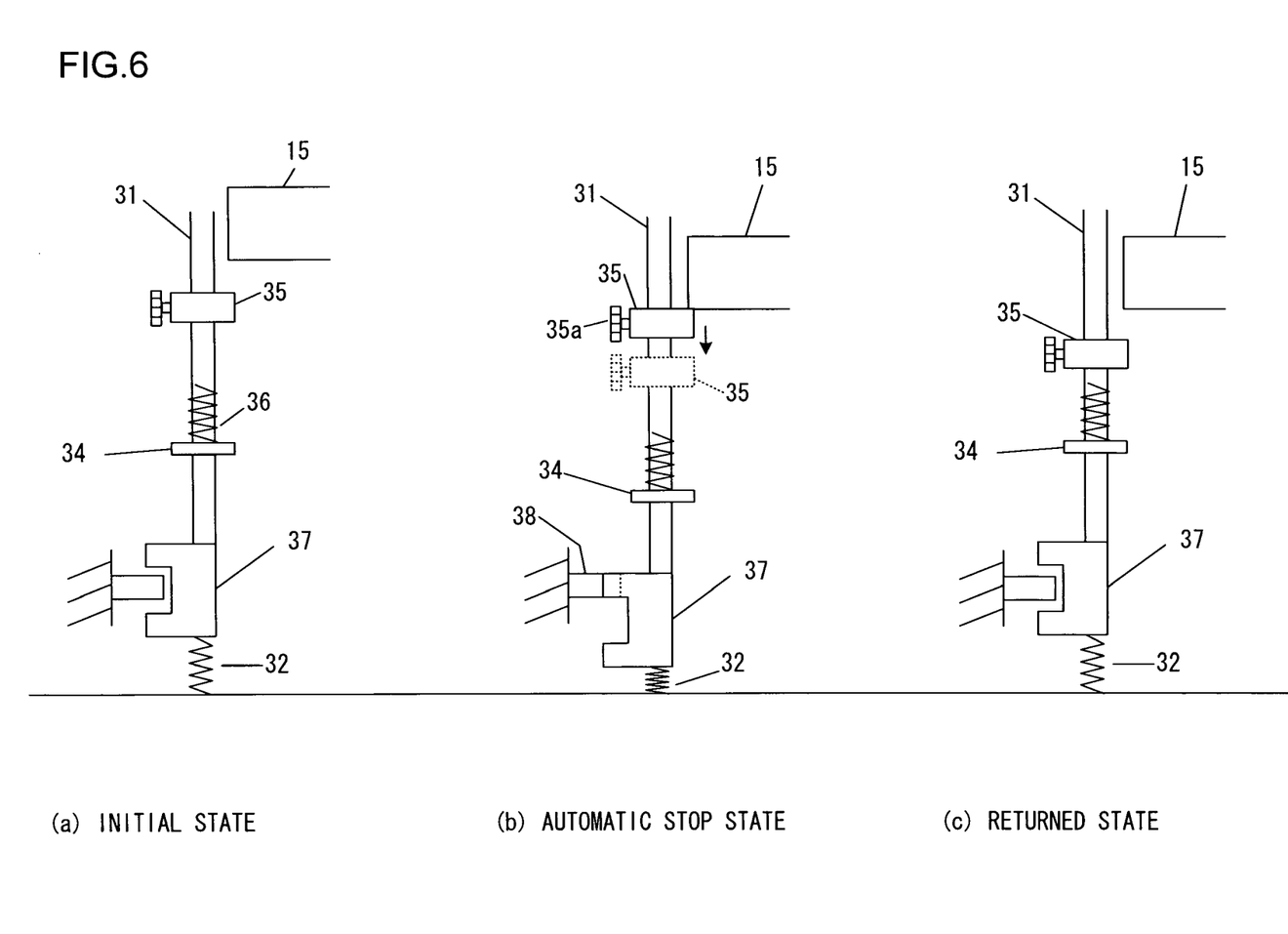
FIG. 6 is a diagram showing an example of the operation of the machine according to one embodiment.

First, explanation is made to a case where tests are performed in a state that the striker 35 is set so as to be sufficiently separated from the restriction member 34 as shown in FIG. 6(a). The crosshead 15 is lowered as driven by the motor 14. When the lower end surface of the crosshead 15 comes in contact with the striker 35 as shown in FIG. 6(b), a pressing force is urged to the movable shaft 31 through the striker 35 and the movable shaft 31 is pushed downward against the biasing force of the spring 32. At this time, the dog 37 together with the movable shaft 31 moves downward, and the position sensor 38 outputs an OFF signal (stop signal). As a result, the switch 44 of the relay circuit is turned ON and the driving by the motor 14 is stopped to automatically stop the crosshead 15.

To raise the crosshead 15 from this state, it is necessary to cancel the automatic stop state. On this occasion, the bolt 35a is loosened by operating it from outside the pole cover 25, and the position of the bolt 35a is deviated downward as indicated in the dotted line in FIG. 6(b). As a result, the movable shaft 31 is pushed up by the biasing force of the spring 32, and returns to the initial position as shown in FIG. 6(c) since the pressing force urged to the movable shaft 31 becomes 0. At this time, also the dog 37 together with the movable shaft 31 moves upward, and the position sensor 38 outputs an ON signal (non-stop signal). As a result, the switch 44 of the relay circuit is turned OFF to cancel the state of automatic stop, so that the crosshead 15 can be raised as driven by the motor 14.

Figure 7:
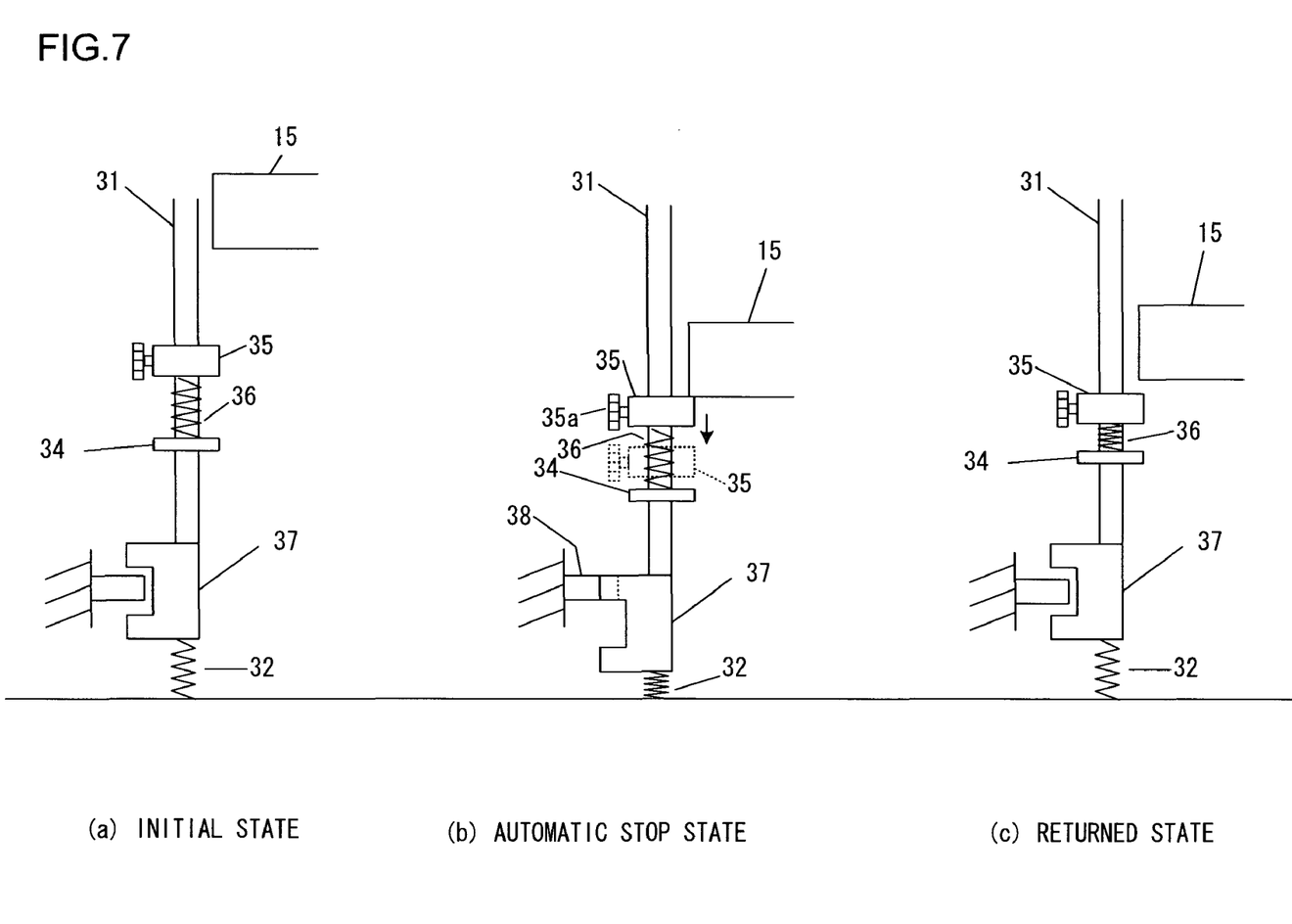
FIG. 7 is a diagram showing another example of the operation of the machine according to one embodiment.

Next, explanation is made on a case where tests are performed in a state that the striker 35 is set to be adjacent to, for instance, at the lower bound position of, the restriction member 34 as shown in FIG. 7(a). When the crosshead 15 is lowered as driven by the motor 14, and the lower end surface of the crosshead 15 comes in contact with the striker 35 as shown in FIG. 7(b), a pressing force is urged to the movable shaft 31 through the striker 35 and the movable shaft 31 is pushed downward against the biasing force of the spring 32. As a result, the position sensor 38 outputs an OFF signal to stop the driving by the motor 14, and the crosshead 15 stops automatically.

To cancel the state of the automatic stop, the bolt 35a is loosened by operating it from outside the pole cover 25 and the bolt 35a is pressed downward as indicated by broken line in FIG. 7(b) to retract the elastic body 36 and deviate the position of the bolt 35a downward. Then, the position of bolt 35a is fixed with the elastic body 36 being retracted. This causes the movable shaft 31 to be pushed up by the biasing force of the spring 32 as shown in FIG. 7 (c) since the pressing force urged on the movable shaft 31 becomes 0, and then, the position sensor 38 outputs an ON signal. As a result, the crosshead 15 can be raised as driven by the motor 14, and the striker 35 can be set to an arbitrary position by loosening the bolt 35a after the crosshead 15 is raised.

Figure 8:
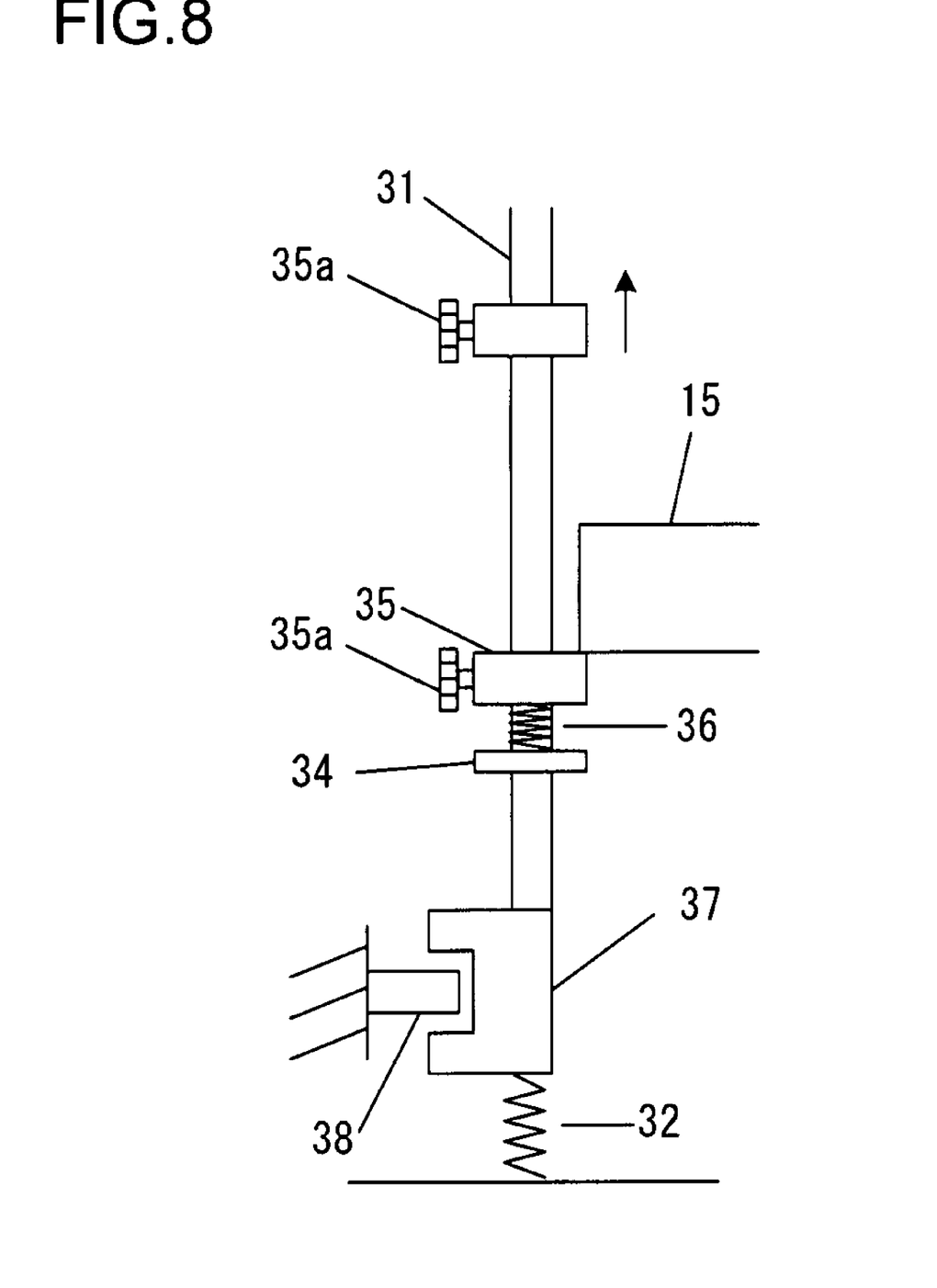
FIG. 8 is a diagram showing a modification of the machine of FIG. 7.

Note that the state of automatic stop (the state indicated by the solid line in FIG. 7(b)) can be cancelled by pushing up the movable shaft 31 with the bolt 35a being loosened. In this case, the lower bolt 35a is locked after the restriction member 34 together with the movable shaft 31 is pushed up by gripping the upper bolt 35a so as to retract the elastic body 36 as shown in FIG. 8. As a result, the movable shaft 31 can be returned to the initial position to cancel the state of automatic stop. Although explanation has been made on the operation of lowering the crosshead 15 as mentioned above, a similar operation takes place when the crosshead 15 is raised.

The following operational effects can be achieved in the embodiment described above.

(1) The elastic body 36 is disposed between the restriction member 34 and the striker 35 to render the striker 35 movable vertically by an extent of elastic deformation from the upper and lower bound positions. As a result, the striker 35 can be spaced from the crosshead 15 without deviation of the restriction member 34 when the crosshead 15 collides with the striker 35 that has been set to the upper or lower bound position to cause the automatic stop to operate. Therefore, the testing machine can be easily returned to the initial state from the state of the automatic stop.

(2) The automatic stop position that is peculiar to the testing machine is never erroneously set since the restriction member 34 need not be deviated, so that the crosshead 15 can surely be prevented from moving beyond the upper and lower bound positions.

(3) Since the relay switch 43 is opened to stop the driving by the motor 14 directly, high safety is obtained.

(4) Since the bolt 35a is provided to the striker 35 so as to project therefrom through the pole cover 25, the position of the striker 35 can be easily changed by operating the bolt 35a from outside the pole cover 25.

(5) Since the bolt 35a is also a member for the positional fixation of the striker 35, the number of parts can be reduced.

(6) Since the spring constant of the elastic body 36 is set greater than that of the spring 32, a big external force is needed to set the strikers 35 at positions exceeding the upper and lower bound positions. As a result, the strikers 35 may be prevented from being set at positions exceeding the upper and lower bound positions.

Although the spring constant of the elastic body 36 is made greater than that of the spring 32 in the above-mentioned embodiment, the former may be made smaller than the latter if a maximum compression amount of the spring is appropriately selected. If the spring constant of the elastic body 36 is set greater than the spring constant of the spring 32, it becomes easier to locate the striker 35. This is because when the striker 35 is set, for instance, at the lower bound position, the movable shaft 31 moves downward due to the collision with the crosshead 15 even if the striker 35 is not locked with the bolt 35a. On the contrary, when the spring constant of the striker 35 is made smaller than that of the spring 32, the striker 35 can be deviated downward by a small force when the automatic stop mechanism is operated, so that the operation of returning from the automatic stop is easy.

Figure 9:
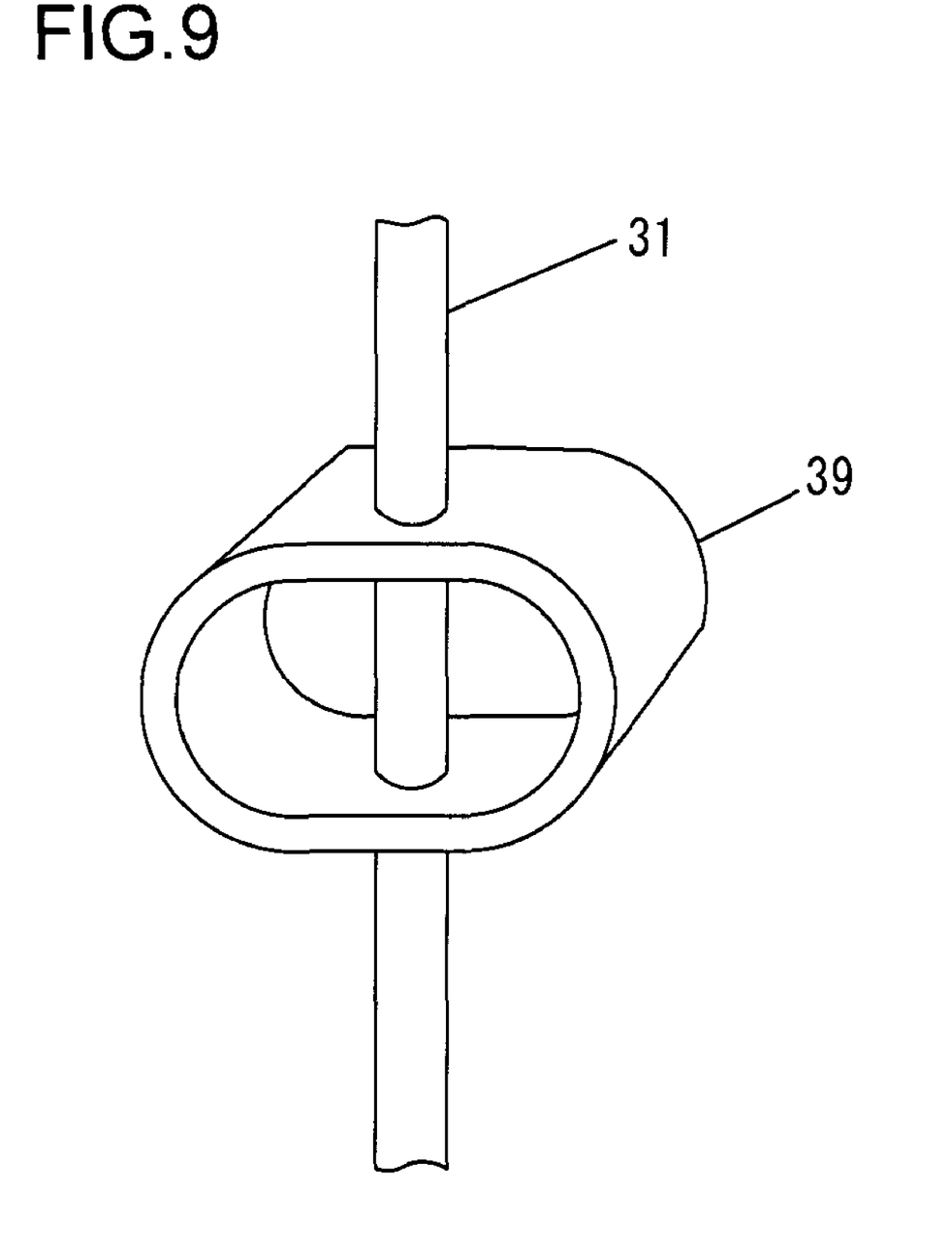
FIG. 9 is a diagram showing a modification of an elastic body.

Although the elastic body 36 is provided between the restriction member 34 and the striker 35 in the above-mentioned embodiment, the elastic body 36 may be provided between the striker 35 and the crosshead 15. The elastic body 36 may be other than a coil spring. For instance, as shown in FIG. 9, a leaf spring 39 that has upper and lower flat surfaces and a curved side surface may be provided between the restriction member 34 and the striker 35 or between the striker 35 and the crosshead 15. The elastic body 36 may be selected from various types of springs such as torsion springs or made of rubbers. That is, any elastic member may be used as far as the striker 35 is supported thereby such that the striker 35 is movable from the upper and lower bound positions relative to the movable shaft 31.

The driving by the motor 14 is automatically stopped by opening the relay switch 44. However, the arrangement of the automatic stop means is not limited thereto. The movable shaft 31 as a moving member is elastically supported to the side of the screw pole 12. However, the movable member is not limited to the above-mentioned one and may be a tabular one. A photo interrupter is used as the position sensor 38. However, the movement of the movable shaft 31 may be detected by other position sensors. The attachment positions are limited by the restriction members 35. However, the limitation member may be provided at parts other than the movable member 31.

The bolt 35a is provided to the striker 35 so as to project therefrom through the pole cover 25 to make it possible to operate the striker 35 by gripping the bolt 35a. However, an operation unit may be provided separately from the bolt 35a, which is a fastening member to lock the striker 35. The movable shaft 31 is disposed inside the pole cover 25. However, the pole cover 25 is not always necessary and the striker 35 may be locked with other locking members.

In the above-embodiment, explanation has been made on the material testing machine in which the crosshead 15 is elevated by rotation of a pair of screw poles 12 as columnar members to apply a load to the specimen piece SP. However, the present invention can be similarly applied to other material testing machines in which a load is applied to the specimen piece SP by other loading means such as, for instance, a hydraulic actuator. Namely, as long as the features and functions of the present invention are realized, the material testing machine according to the present invention is not limited to the examples presented in the above-mentioned embodiments.

The invention claimed is:

1. A material testing machine, comprising:
   a pair of columnar members disposed on both sides of a specimen piece;
   a crosshead, bridging the pair of columnar members, that applies a load to the specimen piece by moving in a direction of a longitudinal axis of the columnar member;
   a movable member disposed at a side of the columnar member, extending in the direction of the longitudinal axis and elastically supported so as to be movable in the direction of the longitudinal axis;
   a striker, integrally attached to the movable member so as to be displaceable in the direction of the longitudinal direction, that is allowed to be pushed by a movement of the crosshead to a position where the striker is attached;
   a position sensor that detects a movement of the movable member by being pushed by the striker;
   a limitation member that limits the position where the striker is attached; and
   an elastic member that supports the striker so that the striker is capable of relative movement in the direction of the longitudinal axis relative to the movable member by a predetermined extent from a position limited by the limitation member.

2. A material testing machine according to claim 1, further comprising:
   an automatic stop means for automatically stopping the crosshead when the movement of the movable shaft is detected by the position sensor.

3. A material testing machine according to claim 2, wherein:
   the limitation member is locked to the movable shaft with a tool to be disposed to a limitation position of an automatic stop position of the crosshead, and
   the elastic member is disposed between the crosshead and the striker or between the striker and the restriction member.

4. A material testing machine according to claim 2, wherein:
   the automatic stop means comprises a relay switch inserted in a motor power supply circuit, and automatically stops the crosshead by opening the relay switch.

5. A material testing machine according to claim 1, further comprising:
   a pole cover that covers both the columnar member and the movable shaft, wherein
   the striker is provided with an operation member with which the striker is operated, the operation member penetrating through the pole cover.

6. A material testing machine according to claim 5, wherein
   the operation member is a fastening member by which the striker is locked.

7. A material testing machine according to claim 3, wherein:
   the automatic stop means comprises a relay switch inserted in a motor power supply circuit, and automatically stops the crosshead by opening the relay switch.

8. A material testing machine according to claim 2, further comprising:
   a pole cover that covers both the columnar member and the movable shaft, wherein
   the striker is provided with an operation member with which the striker is operated, the operation member penetrating through the pole cover.

9. A material testing machine according to claim 3, further comprising:
   a pole cover that covers both the columnar member and the movable shaft, wherein
   the striker is provided with an operation member with which the striker is operated, the operation member penetrating through the pole cover.

10. A material testing machine according to claim 4, further comprising:
    a pole cover that covers both the columnar member and the movable shaft, wherein
    the striker is provided with an operation member with which the striker is operated, the operation member penetrating through the pole cover.

* * * * *